United States Patent [19]

Gareau et al.

[11] Patent Number: 5,750,539
[45] Date of Patent: May 12, 1998

[54] HETEROARYL DIOL ACIDS AS LEUKOTRIENE ANTAGONISTS

[75] Inventors: Yves Gareau, N.D. Ile-Perrot; Claude Dufresne, Dollard Des Ormeaux; Marc Labelle, Ile-Perrot; James Yergey, St. Lazare, all of Canada; Xin Xu, North Wales, Pa.; Deborah Nicoll-Griffith, Baie d' Urfe, Canada; Nathalie Chauret, Dollard des Ormeaux, Canada; Laird Trimble, Pierrefonds, Canada

[73] Assignee: Merck Frosst Canada, Kirkland, Canada

[21] Appl. No.: 475,139

[22] Filed: Jun. 7, 1995

[51] Int. Cl.$^6$ .................. A61K 31/47; C07D 215/12
[52] U.S. Cl. .................. 514/311; 546/174; 546/114; 514/301
[58] Field of Search .................. 546/174, 176, 546/114; 514/228, 311, 301

[56] References Cited

U.S. PATENT DOCUMENTS

| | | | |
|---|---|---|---|
| 5,266,568 | 11/1993 | Belley et al. | 514/228.2 |
| 5,270,324 | 12/1993 | Zamboni et al. | 514/311 |
| 5,350,760 | 9/1994 | Labelle et al. | 514/367 |
| 5,428,033 | 6/1995 | Belley et al. | 514/228.2 |
| 5,438,141 | 8/1995 | Labelle et al. | 546/176 |

FOREIGN PATENT DOCUMENTS

| | | |
|---|---|---|
| 315399 | 10/1989 | European Pat. Off. . |
| 348155 | 12/1989 | European Pat. Off. . |
| 399818 | 11/1990 | European Pat. Off. . |
| 480717 | 4/1992 | European Pat. Off. . |
| 604114 | 6/1994 | European Pat. Off. . |

OTHER PUBLICATIONS

Chauret, et al In Vitro Biotransformations of MK–0476, A New Potent LTD4 Antagonists, Presented at the 10th International Symposium on Microsomes & drug Oxidations, Toronto, Canada Jul. 18–21 1994.

U.S. application No. 07/866,697, Apr. 13, 1992, Gauthier, J.Y., et al (Our Case 18720).

Primary Examiner—C. Warren Ivy
Assistant Examiner—Charanjit S. Aulakh
Attorney, Agent, or Firm—Mollie M. Yang; David L. Rose

[57] ABSTRACT

Compounds of Formula I:

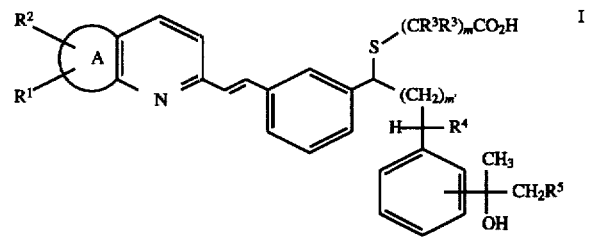

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

8 Claims, No Drawings

HETEROARYL DIOL ACIDS AS LEUKOTRIENE ANTAGONISTS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

Recently a number of compounds of formula (a) in which A represents optionally substituted heterocycle, and pharmaceutically acceptable salts thereof, have been disclosed as leukotriene antagonists and inhibitors of leukotriene biosynthesis.

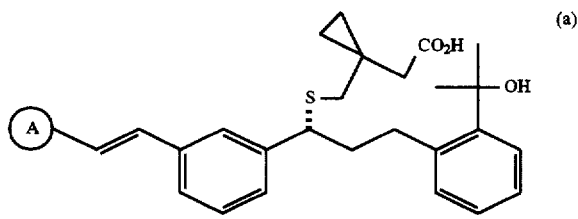

(a)

EP 480,717 discloses compounds of formula (a) in which A represents optionally substituted quinoline; more specifically disclosed is the compound in which A represents 7-chloro-2-quinolinyl. U.S. Pat. No. 5,270,324 discloses two compounds of formula (a) in which A represents 6-fluoro- or 6,7-difluoro-2-quinolinyl. EP Published Application 604, 114 discloses compounds in which A is halo-substituted thienopyridine, particularly 2,3-dichlorothieno[3,2-b]pyridin-5-yl.

SUMMARY OF THE INVENTION

The present invention relates to unsaturated heteroaryl diol acid compounds having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compounds of the invention are best realized by the Formula I:

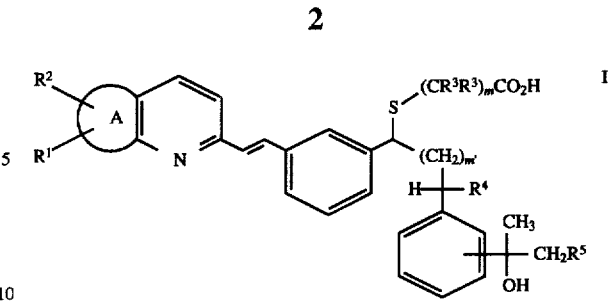

I wherein

A and the pyridine ring to which it is fused together represent quinolinyl or thienopyridinyl;

$R^1$ and $R^2$ are independently hydrogen or halogen;

$R^3$ is H, lower alkyl, $CF_3$ or two $R^3$ groups joined to the same carbon form a 3- to 5-membered carbocyclic ring one of $R^4$ and $R^5$ is H and the other is OH;

m is 1 to 5;

m' is 1 or 2;

or a pharmaceutically acceptable salt thereof.

In one preferred embodiment, the bicyclic heterocylic fragment

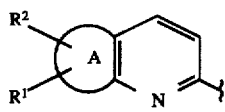

is selected from quinoline and thieno[3,2-b]pyridine. More preferred are substituted bicyclic heterocycles selected from 7-chloroquinolin-2-yl, 6,7-difluoroquinolin-2-yl and 2,3-dichlorothieno[3,2-b]pyridin-5-yl.

In another preferred embodiment, $(CR^3R^3)_m$ represents —$CH_2C(CH_2CH_2)CH_2$—.

Another preferred embodiment provides compounds of formula I in which $R^4$ is H and $R^5$ is OH.

Yet another preferred embodiment provides compounds of formula I in which $R^5$ is H and $R^4$ is OH.

In the application "lower alkyl" includes linear, branched and cyclic structures of from 1 to 7 carbon atoms. Examples of lower alkyl groups include methyl, ethyl, propyl, isopropyl, butyl, s- and t-butyl, pentyl, hexyl, heptyl, and the like.

Halogen includes F, Cl, Br, and I.

When a variable occurs more than once in a molecule, each occurrence of that variable is defined independently of the others. For example $CR^3R^3$ may be —CH2—, —CHCH3—, etc, and $(CR^3R^3)_3$ may represent —$CH_2C(CH_2CH_2)CH_2$—.

Abbreviations

Ac=acetyl
DMAP=4-(dimethylamino)pyridine
DMF=N,N-dimethylformamide
DMSO=dimethyl sulfoxide
EA (EtOAc)=ethyl acetate
Hex=hexane
$NEt_3$=triethylamine
Ms=methanesulfonyl=mesyl
NBS=N-bromosuccinimide
NSAID=non-steroidal anti-inflammatory drug
Ph=phenyl
PPTS=pyridinium para-toluenesulfonate
r.t.=room temperature
rac.=racemic TFA=trifluoroacetic acid
THF=tetrahydrofuran
TLC=thin layer chromatography
Tol=toluene

Alkyl Group Abbreviations

Me=methyl
Et=ethyl
n—Pr=normal propyl
i—Pr=isopropyl
n—Bu=normal butyl
i—Bu=isobutyl
s—Bu=secondary butyl
t—Bu=tertiary butyl
c—Pr=cyclopropyl
c—Bu=cyclobutyl
c—Pen=cyclopentyl
c—Hex=cyclohexyl

Optical Isomers—Diastereomers—Geometric Isomers

Compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases, or acids including inorganic and organic acids.

Salts derived from inorganic bases include aluminum, ammonium, calcium, copper, ferric, ferrous, lithium, magnesium, manganic salts, manganous, potassium, sodium, zinc, and the like.

Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Salts derived from pharmaceutically acceptable non-toxic inorganic and organic acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation, and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia, and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and day, and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives,
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO—Na+or —CH$_2$CH$_2$COO—Na+), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO—Na+), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

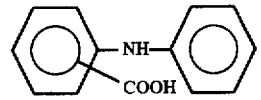

which can bear a variety of substituents and in which the free —COOH group can be in the form of a pharmaceutically acceptable salt group, e.g., —COO—Na+.

The biphenylcarboxylic acid derivatives which can be used comprise: diflunisal and flufenisal. Structurally related biphenyl-carboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

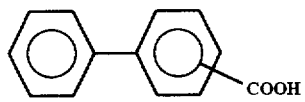

which can bear a variety of substituents and in which the free —COOH group can be in the form of a pharmaceutically acceptable salt group, e.g., —COO—Na+.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

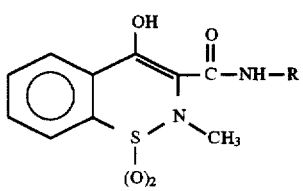

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058, 785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethyl-histidine, described in U.S. Pat. No. 4,325, 961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K+/H+ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, 316, 126–131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods.

SCHEME 1

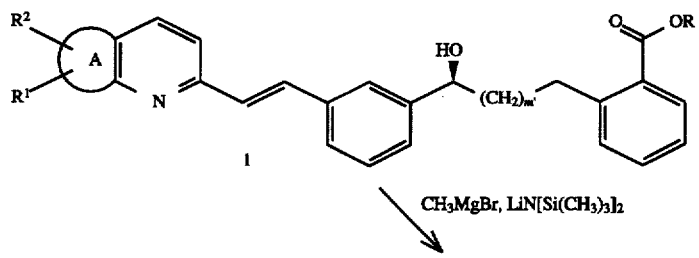

-continued
SCHEME 1

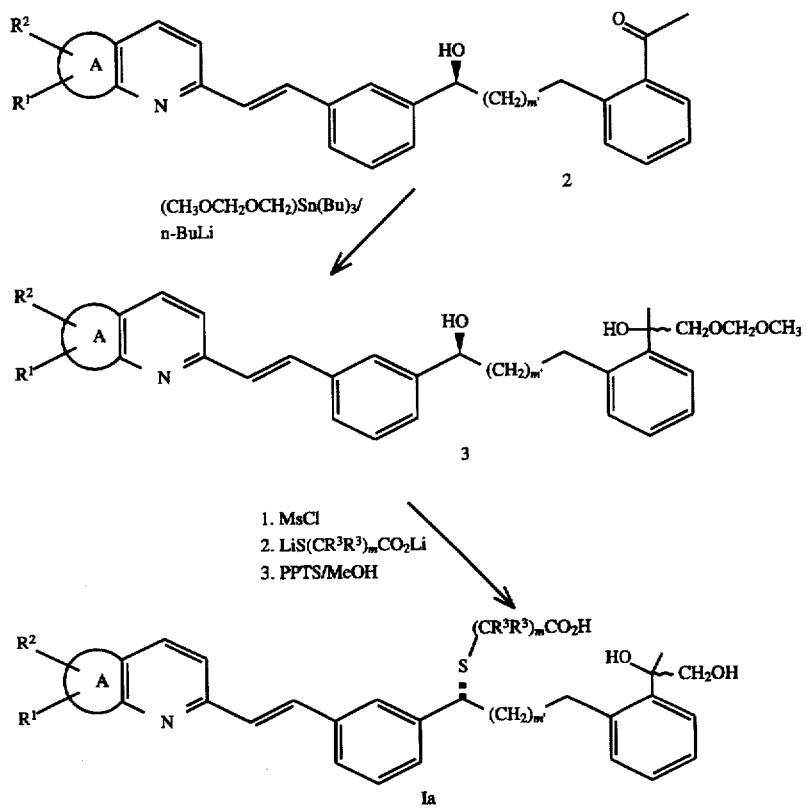

In Scheme 1, R is lower alkyl. The ester 1 is converted to the corresponding methyl ketone 2 using standard reagents such as methyl magnesium bromide and lithium hexamethyldisilazide. The ketone 2 is then treated with (methoxymethoxymethyl)tributylstannane/n-butyllithium to provide the mono-methoxymethyl (MOM) protected triol 3. Conversion of the secondary hydroxyl group of 3 to a leaving group such as the methanesulfonate, followed by displacement with the mercaptoalkanoic acid dianion provides MOM-protected Ia. The MOM protecting group may be removed by pyridinium p-toluenesulfonate to give a diastereomeric mixture of Ia, which may then be separated using chromatographic techniques such as using a chiral column. More preferably, Ia or protected Ia is converted into an ester, for example the methyl ester using diazomethane, followed by MOM deprotection, if necessary; the diastereomeric mixture of the ester is then subject to separation, and the separated diastereomers are then hydrolyzed to give the desired acids Ia.

SCHEME 2

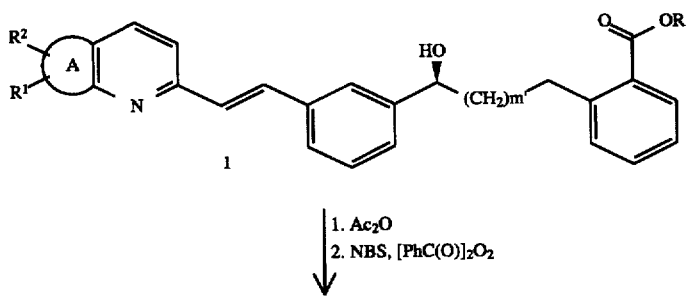

-continued
SCHEME 2

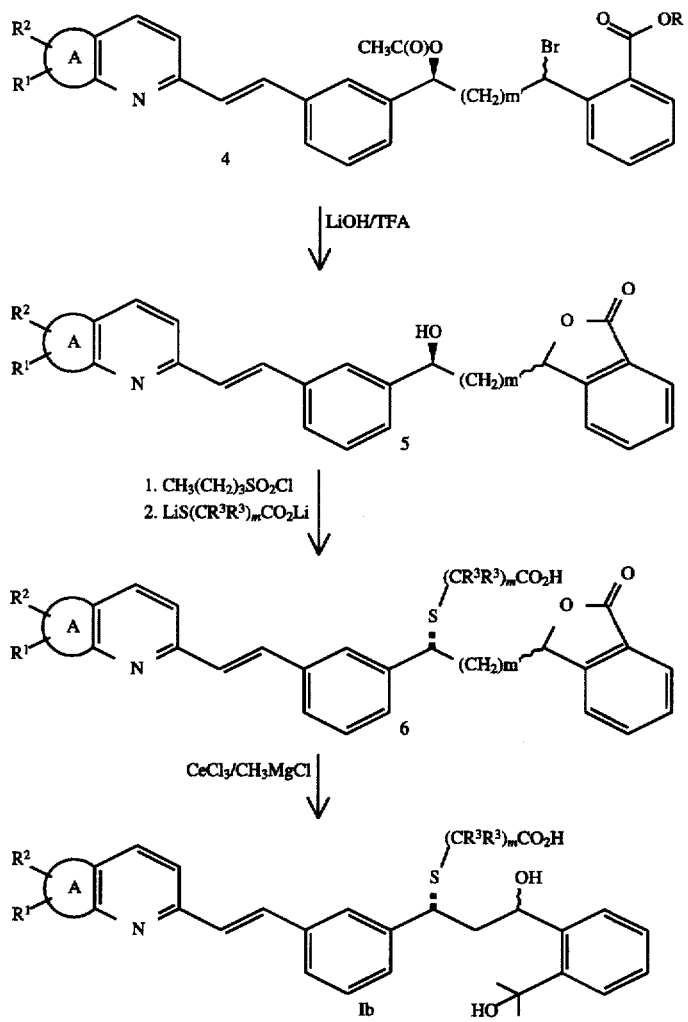

In Scheme 2, R is lower alkyl. The secondary hydroxyl group of ester 1 is first protected, for example by acetylation, followed by bromination at the available benzylic carbon using N-bromosuccinimide and benzoyl peroxide to provide bromo ester 4. Hydrolysis of the ester in the presence of a base such as lithium hydroxide provide the bicyclic lactone 5, after acid treatment. Conversion of the secondary hydroxyl group of 5 to a leaving group such as the butanesulfonate, followed by displacement with the mercaptoalkanoic acid dianion provides thiolated lactone 7. Cerium chloride and methylmagnesium bromide are used to provide the diol Ib as a diasteromeric mixture, which can then be chromatographically separated into the individual diastereomers.

Compounds of formula I are metabolites of compounds of formula Ic. Therefore, in addition to chemical synthesis, compounds of formula I can also be isolated from plasma of individuals to whom a compound of formula Ic has been administered, using methodologies that are well known in the art.

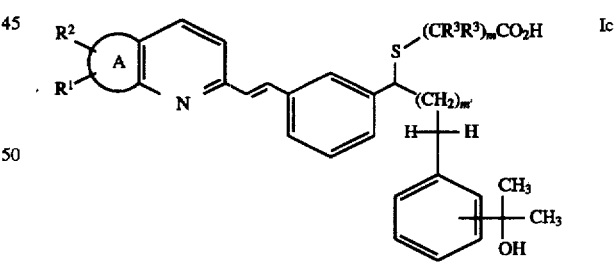

Assays for Determining Biological Activity

The leukotriene antagonist properties of the compounds of the present invention are evaluated using the following assays:

1. [$^3$H]LTD$_4$ Receptor Binding Assay in DMSO-differentiated U937 Cells (a human monocytic cell line);
2. [$^3$H]LTD4 Receptor Binding on Guinea Pig Lung Membranes;
3. [$^3$H]LTD4 Receptor Binding on Human Lung Membranes;
4. In Vitro Guinea Pig Trachea; and
5. In Vivo Assays in Anesthetized Guinea Pigs.

The above assays are described by T. R. Jones et al., Can. J. Physiol. Pharmacol. 1991, 69, 1847–1854.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyzer, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 µg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., *Prostaglandins*, 28, 173–182 (1984) and McFarlane, C. S. et al., *Agents Actions*, 22, 63–68 (1987).)

Prevention of Induced Bronchoconstriction in Allergic Sheep

A. Rationale: Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods: *Animal Preparation*: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.); and b) they have previously responded to inhalation challenge with *Ascaris suum* with both an acute bronchoconstriction and a late bronchial obstruction (W. M. Abraham et al., *Am. Rev. Resp. Dis.*, 128, 839–44 (1983)).

*Measurement of Airway Mechanics:* The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP- 11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention will now be illustrated by the following non-limiting examples in which, unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used: v (volume), w (weight), b.p. (boiling point), m.p. (melting point), L (liter(s)), ML (milliliters), g (gram (s)), mg (milligram(s)), mol (moles), mmol (millimoles), eq. (equivalent(s)).

EXAMPLE 1

(R,R or S)-1-((((3-(2-(7-chloro-2-quinolinyl)-(E)-ethenyl)phenyl)-3-(2-(1,2-dihydroxy-1-methylethyl)phenyl)propyl)thio)methyl)cyclopropane acetic acid Step 1

(S)1-(2-(3-(3-(2-(7—Chloro-2-quinolinyl)-(E)-ethenyl)phenyl)-3-hydroxypropyl)phenyl)ethanone To a solution of lithium bis(trimethylsilyl)amide (355 ml, 352 mmol, 1M in THF) at −15° C. was added dropwise methylmagnesium chloride (59.3 ml, 178 mmol, 3 M in THF ). The reaction mixture was warmed to 0° C. and stirred for 1 h . The methylmagnesiate reagent was then added over 1 h to a solution of methyl (S)-2-(3-(3-(2-(7-chloro-2-quinolinyl)-(E)-ethenyl)phenyl)(1-hydroxypropyl)) benzoate ( see U.S. Pat. No. 5,270,324, 25.0 g, 54.6 mmol) in toluene (150 ml) at −200° C. The reaction mixture was warmed to 0° C. for 3 h. The mixture was poured into 2.4M $NH_4Cl$ solution ($H_2O$/HOAc 20%, 2 L) and extracted with EtOAc (2×500 ml). The combined EtOAc fractions were dried over anhydrous $MgSO_4$. Flash chromatography of the concentrated extract on silica gel (Tol/EtOAc 20%) gave 19.0 g of the title compound. $^1$H NMR (400 MHz, acetone-$d_6$) δ 2.04 (m, 2H), 2.56 (s, 3H), 2.89–2.96 (m, 1H), 3.00–3.07 (m, 1H), 4.40 (d, J=4.2 Hz, 1H), 4.75 (m, 1H), 7.28–7.60 (m, 8H), 7.75 (s, 2H), 7.83–8.00 (m, 4H), 8.33 (d, J=8.6 Hz, 1H).

Step 2

(S)-1-(2-(3-(3-(2-(7-Chloro-2-quinolinyl)-(E)-ethenyl) phenyl) (1-hydroxypropyl))phenyl)-1-(methoxymethoxymethyl) ethanol To a solution of ((methoxymethoxy)methyl) tributylstannane (22.3 g, 61.1 mmol) in THF (100 ml) at −78° C. was added n-butyllithium (23.3 ml, 58.2 mmol )

over 10 min. A solution of the starting ketone from step 1 (7.20 g, 16.3 mmol ) in THF (20 ml) at −78° C. was canulated slowly. The mixture was stirred for 1 h at −780° C. Aqueous NH$_4$Cl (25%) was added directly into the reaction mixture and extracted with EtOAc. Flash chromatography of the crude product on silica gel (Hex/AcOEt 40%) gave 2.70 g of the title compound as a diastereomeric mixture. $^1$H NMR (400 MHz, CDCl$_3$) δ 1.64 (m, 3H), 2.15 (m, 2H), 3.00–3.30 (m, 3H), 3.33 (s, 3H), 3.42–3.48 (m, 1H), 3.62 (d, J=10 Hz, 1H), 3.98 (d, J=10 Hz, 1H), 3.73 (d, J=10 Hz, 1H), 4.05 (d, J=10 Hz, 1H), 4.69–4.70 (m, 3H), 7.15–7.43 (m, 7H), 7.49 (m, 1H), 7.60–7.71 (m, 5H), 8.05–8.09 (m, 2H).

Step 3

(R,R or S)-1-((((3-(2-(7-chloro-2-quinolinyl)-(E)-ethenyl) phenyl)-3-(2-(1-(methoxymethoxymethyl)ethanol)phenyl) propyl)thio)methyl)cyclopropaneacetic acid (a) To a solution of the diol from step 2 (170 mg, 0.33 mmol) in 1 mL Tol/CH$_3$CN 1:1 was added diisopropylethylamine (60.9 μL, 0.34 mmol ). The reaction mixture was cooled to −48° C., then methanesulfonyl chloride (25.8 μL, 0.33 mmol) was added slowly. The temperature was raised to −20° C. and maintained for 1 h. The cold solution was poured into saturated aqueous NaHCO$_3$ and extracted with EtOAc.

The combined extracts were dried over Na$_2$SO$_4$, concentrated and used as such for the next step. $^1$H NMR (400 MHz, CDCl$_3$) δ 1.55 (s, 3H), 2.20–2.32 (m, 1H), 2.38–2.49 (m, 1H), 2.76 (s, 3H), 2.94–3.11 (m, 1H), 3.12–3.20 (m, 2H), 3.30 (s, 3H), 3.59–3.64 (m, 1H), 3.89–3.96 (m, 1H), 4.66 (m, 2H), 5.67 (m, 1H), 7.10–7.49 (m, 8H), 7.61–7.74 (m, 5H), 8.09–8.15 (m, 2H).

(b) To 1-(mercaptomethyl)cyclopropaneacetic acid (48.6 mg, 0.33 mmol) in degassed THF (0.45 ml ) cooled at −15° C. was added slowly a solution of n-butyllithium (265 μL, 0.66 mmol, 2.5 M in Hex) over 10 min. The heterogeneous mixture was warmed to −8° C. for 30 min. The crude mesylate from (a) in THF (0.5 ml) was added to the mercapto acid suspension and stirred at −15° C. overnight. Aqueous NH$_4$Cl (25%) was added and the mixture was extracted with EtOAc. Flash chromatography (Hex/EtOAc 30%/AcOH 1%) gave 100 mg of the title product. $^1$H NMR (400 MHz, CDCl$_3$) δ 0.46–0.57 (m, 4H), 1.53 (s, 3H), 2.15–2.25 (m, 2H), 2.26–2.36 (m, 2H), 2.57–3.06 (m, 3H), 3.07–3.14 (m, 1H), 3.29 (s, 3H), 3.60–3.64 (m, 1H), 3.93–4.02 (m, 2H), 4.66 (m, 2H), 7.10–7.80 (m, 13H), 8.03–8.11 (m, 2H).

Step 4

Methyl (R,R or S)-1-((((3-(2-(7-chloro-2-quinolinyl)-(E)-ethenyl)phenyl)-3-(2-(1,2-dihydroxy-1-methylethyl) phenyl)propyl)thio) methyl)cyclopropaneacetate To a solution of the acid of step 3 (1.000 g, 1.55 mmol) in 10 mL of Et$_2$O was added a standard solution of diazomethane until TLC showed total consumption of starting material. The mixture was evaporated to dryness and was then dissolved in 35 mL of tert-butanol. PPTS (3.89 g, 15.5 mmol) was added and the mixture was refluxed for 12 h. It was poured in 250 mL aqueous NH$_4$OAc (25%) and extracted with 100 mL Et$_2$O. The organic phase was washed with 100 mL water, dried over Na$_2$SO$_4$, filtered and concentrated. Flash chromatography (Tol/EA 30%) afforded the title compounds (550 mg, 58%) along with 300 mg of the methyl ester intermediate. The two diastereoisomers were separated by HPLC on a CHIRALPAK AD praparative column using ethanol as the eluent. From 25 mg of the diastereomeric mixture was obtained 11.8 mg of the title compound (RT=44min). $^1$H NMR (400 MHz, acetone-d$_6$) δ 0.38–0.53 (m, 4H), 1.51 (s, 3H), 2.23 (dd, J=16.3, 7.6 Hz, 2H), 2.39 (d, J=15.9 Hz, 1H), 2.46 (d, J=15.9 Hz, 1H), 2.55 (s, 2H), 2.85–2.92 (m, 1H), 3.05–3.11 (m, 1H), 3.57 (s, 3H), 3.63 (d, J=10.8 Hz, 1H), 3.89 (d, J=10.8 Hz, 1H), 4.05 (t, J=7.4 Hz, 1H), 7.06–7.17 (m, 3H), 7.39–7.44 (m, 3H), 7.52–7.56 (m, 2H), 7.62–7.64 (m, 1H), 7.79 (s, 1H), 7.87–7.96 (m, 3H), 8.04 (s, 1H), 8.35 (d, J=8.6 Hz, 1H).

Step 5

(R,R/S)-1-((((3-(2-(7-chloro-2-quinolinyl)-(E)-ethenyl) phenyl)-3-(2-(1,2-dihydroxy- 1-methylethyl)phenyl)propyl) thio)methyl)cyclopropaneacetic acid To a solution of the compound from step 4 (10.1 mg, 0.016 mmol) in 0.25 mL of ethanol was added 0.033 mL of aqueous NaOH (1N). The mixture was stirred at 60° C. for 4 h, then cooled and acidified with 0.02 ml of AcOH. This was then diluted with 1 mL H$_2$O, and 2 mL of EA. The organic extracts were dried over Na$_2$SO$_4$, filtered and concentrated to afford the title compound (6.5 mg, 66%). NMR (400 MHz, acetone d$_6$) δ 0.38–0.56 (m, 4H), 1.51 (s, 3H), 2.19–2.27 (m, 2H), 2.44 (s, 2H), 2.60 (s, 2H), 2.83–2.97 (m, 1H), 3.08–3.15 (m, 1H), 3.63 (d, 10.8 Hz, 1H), 3.76 (d, J=10.8 Hz, 1H), 4.08 (t, 7.35 Hz, 1H), 7.05–7.19 (m, 4H), 7.39–7.62 (m, 5H), 7.80–8.02 (m, 5H), 8.33 (d, 8.6 Hz, 1H).

EXAMPLE 2

(R,S or R)-1-((((3-(2-(7-chloro-2-quinolinyl)-(E)-ethenyl)phenyl)-3-(2-(1,2-dihydroxy-1-methylethyl) phenyl)propyl)thio)methyl) cyclopropaneacetic acid Step 1

Methyl-(R,S or R)-1-((((3-(2-(7-chloro-2-quinolinyl)-(E)-ethenyl)phenyl)-3-(2-(1,2-dihydroxy-1-methylethyl) phenyl)propyl)thio) methyl)cyclopropaneacetate The column of step 4, Example 1 was further eluted to give 8.1 mg of the second diastereoisomer (RT=51 min). $^1$H NMR (400 MHz, acetone-d$_6$) δ 0.38–0.53 (m, 4H), 1.51 (s, 3H), 2.20–2.29 (m, 2H), 2.39 (d, J=15.8 Hz, 1H), 2.46 (d, J=15.8 Hz, 1H), 2.55 (s, 2H), 2.81–2.88 (m, 1H), 3.09–3.12 (m, 1H), 3.57 (s, 3H), 3.63 (d, J=10.8 Hz, 1H), 3.76 (s, J=10.8 Hz, 1H), 4.05 (t, J=6.6 Hz, 1H), 7.06–7.16 (m, 3H), 7.39–7.43 (m, 3H), 7.53–7.57 (m, 2H), 7.62–7.64 (m, 1H), 7.80 (s, 1H), 7.88–7.97 (m, 3H), 8.05 (s, 1H), 8.35 (d, J=8.6 Hz, 1H).

Step 2

To a solution of the compound from step 1 (5.2 mg, 0.0084 mmol) in 0.15 mL of ethanol was added 0.016 mL of aqueous NaOH (1N). The mixture was stirred at 60° C. for 4 h, then cooled and acidified with 0.01 ml of AcOH. This was then diluted with 1 mL H$_2$O, and 2 mL of EA. The organic extracts were dried over Na$_2$SO$_4$, filtered and concentrated to afford the title compound (3.5 mg, 70%). NMR (400 MHz,acetone d$_6$) δ 0.39–0.55 (m, 4H), 1.51 (s, 3H), 2.16–2.30 (m, 2H), 2.44 (s, 2H), 2.60 (s, 2H), 2.80–2.88 (m, 1H), 3.10–3.17 (m, 1H), 3.63 (d, 10.8 Hz, 1H), 3.76 (d, 10.8 Hz, 1H), 4.08 (t, 7.8 Hz, 7.0 Hz, 1H), 7.04–7.19 (m, 4m), 7.39–7.60 (m, 5H), 7.80–8.02 (m, 5H), 8.33 (d, 8.6 Hz, 1H).

EXAMPLE 3

(R,R or S) and (R, S or R)-1-((((3-(2-(7-chloro-2-quinolinyl)-(E)-ethenyl)phenyl)-3-(2-(1,2-dihydroxy- 1-methylethyl)phenyl)propyl)thio) methyl)cyclopropaneacetic acid:

The title compounds are prepared following the procedures of Examples 1 and 2, and substituting methyl (S)-2-(3-(3-(2-(6,7-difluoro-2-quinolinyl)-(E)-ethenyl)phenyl)(1- hydroxypropyl))benzoate (see U.S. Pat. No. 5,270,324) for methyl (S)-2-(3-(3-(2-(7-chloro-2-quinolinyl)-(E)-ethenyl) phenyl)(1-hydroxypropyl))benzoate in Step 1.

EXAMPLE 4

(R,R or S) and (R,S or R)-1-((((3-(2-(2,3-dichlorothieno[3,2-b]pyridin-5-yl)-(E)-ethenyl) phenyl)-3-(2-(1,2-dihydroxy-1-methylethyl)phenyl) propyl) thio)methyl)cyclopropaneacetic acid The title compounds are prepared following the procedures of Examples 1 and 2, and substituting methyl (S)-2-(3-(3-(2-(2,3-dichlorothieno[3,2-b]pyridin-5-yl)-(E)-ethenyl)phenyl)(1-hydroxypropyl))benzoate (see EP 604, 114) for methyl (S)-2-(3-(3-(2-(7-chloro-2-quinolinyl)-(E)-ethenyl)phenyl)(1-hydroxypropyl))benzoate in Step 1.

EXAMPLE 5

1((((3-(2-(7-Chloro-2-quinolinyl)-(E)-ethenyl) phenyl)- (1R,3S)-3-(2-(1-hydroxy-1-methylethyl) phenyl)-3-hydroxypropyl) thio)methyl) cyclopropaneacetic acid $C_{30}H_{26}ClNO_4$: C, 72.07; H, 5.24; N, 2.80; found: C, 71.48; H, 5.29; N, 2.84.

Step 2

Methyl 2-(3-(3-(2-(7-chloro-2-quinolinyl)-(E)-ethenyl) phenyl)-(1R/S, 3S)-3- acetoxy-1-bromopropyl)benzoate To a solution of the compound from Step 1 (26.30 g, 52.6 mmol) in 1.30 L of $CCl_4$ was added N-bromosuccinimide (9.93 g, 55.8 mmol) followed by benzoyl peroxide (923 mg, 3.81 mmol). The mixture was refluxed for 3 h, cooled to r.t. then poured into 200 mL of saturated aqueous $NaHCO_3$. The organic layer was separated, the aqueous phase was washed with (2×100 mL) $CH_2Cl_2$. The combined organic extracts were dried over $Na_2SO_4$, filtered and concentrated. Flash chromatography (Tol/$Et_2O$ 5%) afforded a mixture 21.00 g (69%) of the desired diastereoisomers (1:1) along with 4.12 g (16%) of starting material. This mixture was used without further purification. An analytical sample of the 1:1 mixture of diastereoisomers was obtained by repeated flash chromatography (Tol/$Et_2O$ 5%).: $^1$H NMR (400 MHz, acetone-$d_6$) δ 2.06 (s, 3H), 2.08 (s, 3H), 2.78–2.87 (m, 3H), 2.96–3.04 (m, 1H), 3.78 (s, 3H), 3.90 (s, 3H), 5.72 (dd, J=8.30, 5.70 Hz, 1H), 6.08 (dd, J=8.14, 5.24 Hz, 1H), 6.30 (t, J=7.76, 7.51 Hz, 1H), 6.43 (dd, J=8.31, 6.06 Hz, 1H), 7.32–7.47 (m, 10H), 7.51–7.66 (m, 4H), 7.70–7.73 (m, 4H), 7.82–7.93 (m,

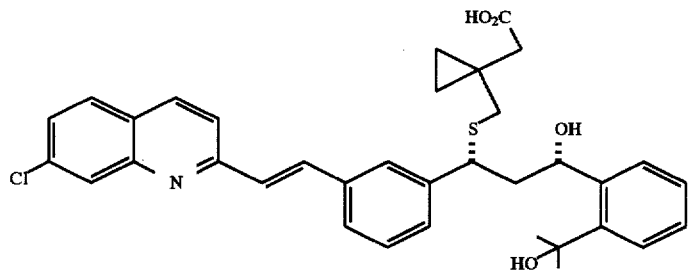

Step 1

Methyl-(S)-2-(3-(3-(2-(7-chloro-2-quinolinyl)-(E)-ethenyl) phenyl)-3-acetoxypropyl)benzoate Methyl-(S)-2-(3-(3-(2-(7-chloro-2-quinolinyl)-(E)-ethenyl)phenyl)-3-hydroxypropyl)benzoate.$H_2O$ (25.10 g, 52.7 mmol) was dried by codistillation with 2×250 mL of toluene. To the residue suspended in 100 mL of $CH_2Cl_2$ was added $Ac_2O$ (8.50 mL, 116 mmol) then $NEt_3$ (8.80 mL, 63.5 mmol). DMAP (321 mg, 2.63 mmol) was added and the reaction mixture became homogeneous within 30 sec. The final mixture was stirred 15 min then poured into 200 mL of saturated aqueous $NaHCO_3$, extracted with (2×100 mL) $CH_2Cl_2$. The combined organic 20 extracts were washed with 100 mL of 25% aqueous $NH_4Cl$, dried over $Na_2SO_4$, filtered, concentrated and dried in vacuo at 60° C. for 1 h to give 26.40 g (100%) of the desired material. It was used without further purification. An analytical sample was obtained by flash chromatography (Tol/EA 5%).: $^1$H NMR (400 MHz, acetone-$d_6$) δ 2.11 (s, 3H), 2.12–2.30 (m, 2H), 2.96–3.09 (m, 2H), 3.83 (s, 3H), 5.87 (dd, J=7.92, 5.48 Hz, 1H), 7.27 (dd, J=7.49, 1.30 Hz, 1H), 7.29 (d, J=7.31 Hz, 1H), 7.35–7.47 (m, 5H), 7.62 (dt, J=7.38, 1.59, 1.56 Hz, 1H), 7.73 (d, J=1.53 Hz, 1H), 7.74 (d, J=8.59 Hz, 1H), 7.83–7.88 (m, 3H), 7.99 (d, J=2.17 Hz, 1H), 8.21 (d, 1H); $^{13}$C NMR (100 MHz, acetone-$d_6$) δ 21.13, 31.14, 38.77, 52.15, 75.95, 121.00, 126.23, 126.61, 126.90, 127.38, 127.40, 127.62, 128.59, 129.57, 129.71, 130.11, 130.49, 131.33, 131.78, 132.76, 135.45, 135.52, 136.95, 137.48, 142.49, 143.75, 149.39, 157.65, 168.19, 170.31; IR (neat) 3000, 1740, 1600 cm$^{-1}$; [α]$D^{20}$ −19.20 (c=0.0154, $CHCl_3$); Analysis calc'd for 8H), 8.00 (s, 1H), 8.00 (s, 1H), 8.18–8.21 (m, 2H); $^{13}$C NMR (100 MHz, acetone-$d_6$) δ 20.9, 21.0, 45.9, 46.4, 46.7, 47.4, 52.5, 52.6, 74.4, 74.4, 120.9, 121.0, 126.1, 126.3, 126.6, 127.4, 127.4, 127.7, 127.8, 128.5, 128.9, 129.0, 129.1, 129.4, 129.7, 129.7, 129.8, 129.9, 130.0, 130.1, 130.2, 131.0, 131.0, 133.3, 133.5, 135.2, 135.2, 135.5, 136.9, 137.6, 141.0, 141.6, 142.6, 143.2, 149.3, 157.5, 167.6, 170.0, 171.1. Analysis calc'd for $C_3OH_{25}ClBrNO_4$: C, 62.25; H, 4.35; N, 2.42; found: C, 62.26; H, 4.58; N, 2.42.

Step 3

3-(2-(3-(2-(7-Chloro-2-quinolinyl)-(E)-ethenyl)phenyl)-(S) -2-hydroxyethyl)-(R/S)-3H-isobenzofuran-1-one To a solution of 23.38 g of the compound from step 2 in 280 mL THF and 140 mL MeOH was added 140 mL (140 mmol) of a 1N LiOH aqueous solution. The mixture was stirred at r.t. for 24 h. The solution was neutralized using 11.0 mL (143 mol) of TFA and stirring for 2 h. The volatiles were evaporated and the residue was poured in saturated aqueous $NaHCO_3$ (1.0L). The aqueous phase was extracted with 3×500 mL of EA. The combined organic fractions were washed with brine (200 mL), dried over $Na_2SO_4$, filtered and concentrated. Flash chromatography (Tol/EA 20% then Tol/EA/AcOH 1:1:0.01) afforded the desired lactones (9.69 g; 64%): $^1$H NMR (400 MHz, acetone-$d_6$) δ 1.89–1.96 (m, 1H), 2.33–2.52 (m, 3H), 4.65 (d, J=4.08 Hz, 1H), 4.90 (d, J=3.37 Hz, 1H), 5.13–5.17 (m, 2H), 5.51 (dd, J=8.11, 5.31 Hz, 1H), 5.95 (dd, J=10.43, 2.47 Hz, 1H), 7.37–7.52 (m, 8H), 7.56–7.65 (m, 4H), 7.67–7.77 (m, 4H), 7.79–7.93 (m, 10H), 7.98–8.00 (m, 2H), 8.28–8.31 (m, 2H); $^{13}$C NMR (100 MHz, acetone-$d_6$) δ 45.0, 45.9, 70.4, 71.3, 79.1, 79.6, 121.0, 123.1, 123.5, 125.3, 125.8, 125.8, 126.0, 126.6, 126.7, 126.7, 127.0, 127.1, 127.3, 127.4, 127.6, 128.4, 128.5, 129.2, 129.3, 129.6, 129.7, 129.8, 129.8, 130.2, 134.7, 134.8, 135.6, 135.8, 137.1, 137.3, 137.4, 146.1, 147.1, 149.4, 151.1, 151.4, 157.8, 170.3, 170.5.

Step 4

1-(((1-(3-(2-(7-Chloro-2-quinolinyl)-(E)-ethenyl)phenyl)-(R)-2-((R/S)-3-oxo-1,3-dihydroisobenzofuran-1-yl)ethyl)thio)methyl) cyclopropaneacetic acid To a solution of the compound from Step 3 (4.60 g, 10.4 mmol) in 28 mL of $CH_2Cl_2$ at $-200°$ C. was added $NEt_3$ (2.16 mL, 15.5 mmol) then butanesulfonyl chloride (1.61 mL, 12.4 mmol). The mixture was stirred at 0° C. for 1 h then poured in 20 mL of saturated aqueous $NaHCO_3$. The aqueous phase was extracted with 3×25 mL of EA. The combined organic fractions were washed with brine (25 mL), dried over $Na_2SO_4$, filtered and concentrated to afford the desired busylate. It was dissolved in 5 mL of dry THF. To a degassed solution of 1-mercaptomethyl-1-cyclopropaneacetic acid (3.02 g, 20.7 mmol) in 20 mL of dry THF at $-200°$ C. was added dropwise n-BuLi (2.48 M, 16.7 mL, 41.4 mmol). The mixture was stirred at 0° C. for 15 min then cooled back to $-200°$ C. The solution of the busylate was added and the final mixture was stirred at 4° C. for 16 h. The solution was exposed to air at 0° C. for 1 h, then it was poured in 200 mL water and 4.0 mL AcOH. The aqueous phase was extracted with 3×200 mL of EA. The combined organic fractions were washed with brine (200 mL), dried over $Na_2SO_4$, filtered and concentrated to afford after flash chromatography (Tol/EA 10%; Tol/EA 10%/AcOH 1%) the title compound (2.68 mg, 45%).: $^1$H NMR (400 MHz, acetone-$d_6$) δ 0.40–0.55 (m, 8H), 2.20–2.29 (m, 2H), 2.48–2.51 (m, 4H), 2.61–2.80 (m, 6H), 4.29–4.39 (m, 2H), 5.24 (dd, 1H), 5.93 (dd, 1H), 7.34–7.42 (m, 3H), 7.44–7.61 (m, 10H), 7.67–7.78 (m, 6H), 7.81–8.05 (m, 11H), 8.31–8.38 (m, 2H).

Step 5

A suspension of cerium chloride (1.49 g, 6.00 mmol) was heated for 10 h in 15 mL of THF. Methylmagnesium chloride (7.80 mL, 23.5 mmol) was then added to the suspension at 0° C. and 40 min later, the bath was heated to 40° C. A solution of the lactone from step 4 (2.68 g, 4.70 mmol) in 15 mL of THF was added dropwise and the reaction mixture was poured in 25% $NH_4OAc$ (60 mL) containing a few drops of AcOH. The aqueous phase was extracted with EA (2×100 mL) and the combined organic phases dried over $Na_2SO_4$. A first chromatography on silica gel (Tol/EA 40%) removed the less polar triols. Then 1% HOAc was added to the eluent to afford both diol-acids. The mixture of diastereoisomers was separated on μBondapak™ C18 preparative HPLC column (MeOH/$H_2O$ 25%/AcOH 0.1%) to give 783 mg (RT: 9.12 min.) of the title compound. $^1$H NMR (400 MHz, acetone-$d_6$) δ 0.16–0.60 (m, 4H), 1.67 (s, 6H), 2.08–2.13 (m, 2H), 2.27–2.33 (m, 1H), 2.46 (d, J=12.7 Hz, 1H), 2.59 (d, J=14.3 Hz, 1H), 2.79 (d, J=12.7 Hz, 1H), 4.51 (dd, J=11.5, 2.7 Hz, 1H), 6.18 (d, J=9.3 Hz, 1H), 7.06–7.13 (m, 2H), 7.25–7.54 (m, 7H), 7.69–7.85 (m, 4H), 7.95 (s, 1H), 8.19 (d, J=8.6 Hz, 1H); HRMS ($FAB^+$) calc'd for $C_{35}H_{35}ClNO_4SNa_2$ (M+Na): 646.17707, found 646.17688.

EXAMPLE 6

1-((((3-(2-(7-Chloro-2-quinolinyl)-(E)-ethenyl)phenyl)-(1R,3R)-3-(2-(1-hydroxy-1-methylethyl)phenyl)-3-hydroxypropyl)thio)methyl) cyclopropaneacetic acid The HPLC column from Example 5 step 5 was further eluted to give 572 mg (RT: 11.36 min ) the title compound.

$^1$H NMR (400 MHz, acetone-$d_6$) δ 0.28–0.52 (m, 4H), 1.30 (s, 3H), 1.34 (s, 3H), 2.14–2.17 (m, 1H), 2.33 (s, 2H), 2.55–2.66 (m, 1H), 2.69 (m, 2H), 4.45–4.48 (dd, J=10.5, 4.03 Hz, 1H), 5.46 (d, J=8.6 Hz, 1H), 7.04–7.16 (m, 2H), 7.28–7.59 (m, 7H), 7.73–7.84 (m, 4H), 7.95 (s, 1H), 8.19 (d, J=8.6 Hz, 1H); HRMS ($FAB^+$) calc'd for $C_{35}H_{35}ClNO_4SNa_2$ (M+Na): 646.17707, found 646.17688.

EXAMPLE 7

1-((((3-(2-(6,7-Difluoro-2-quinolinyl)-(E)-ethenyl)phenyl)-(1R,3R)- and (1R,3S)-3-(2-(1-hydroxy-1-methylethyl)phenyl)-3-hydroxypropyl)thio) methyl) cyclopropaneacetic acid The title compounds are prepared following the general procedures of Examples 5 and 6, and substituting methyl (S)-2-(3-(3-(2-(6,7-difluoro-2-quinolinyl)-(E)-ethenyl)phenyl)(1-hydroxypropyl))benzoate for methyl (S)-2-(3-(3-(2-(7-chloro-2-quinolinyl)-(E)-ethenyl)phenyl)(1-hydroxypropyl))benzoate in Step 1.

EXAMPLE 8

1-((((3-(2-(2,3-Dichlorothieno[3,2-b]pyridin-5-yl)-(E)-ethenyl)phenyl)-(1R,3R)- and (1R,3S)-3-(2-(1-hydroxy-1-methylethyl)phenyl)-3-hydroxypropyl) thio) methyl) cyclopropaneacetic acid The title compounds are prepared following the general procedures of Examples 5 and 6, and substituting methyl (S)-2-(3-(3-(2-(2,3-dichlorothieno[3,2-b]pyridin-5-yl)-(E)-ethenyl)phenyl)(1-hydroxypropyl))benzoate for methyl (S)-2-(3-(3-(2-(7-chloro-2-quinolinyl)-(E)-ethenyl)phenyl)(1-hydroxypropyl))benzoate in Step 1.

What is claimed is:

1. A compound having the Formula I:

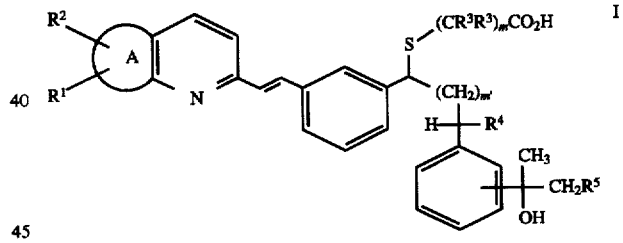

wherein

A and the pyridine ring to which it is fused together represent quinolinyl or thienopyridinyl;

$R^1$ and $R^2$ are independently hydrogen or halogen;

$R^3$ is H, lower alkyl, $CF_3$ or two $R^3$ groups joined to the same carbon form a 3- to 5-membered carbocyclic ring one of $R^4$ and $R^5$ is H and the other is OH;

m is 1 to 5;

m' is 1 or 2;

or a pharmaceutically acceptable salt thereof.

2. A compound of claim 1 wherein the fragment

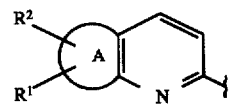

is selected from the group consisting of 7-chloroquinolinyl, 6,7-difluoroquinolinyl and 2,3-dichlorothieno[3,2-b]pyridinyl.

3. A compound of claim 1 wherein $R^4$ is H and $R^5$ is OH.

4. A compound of claim 1 wherein $R^5$ is H and $R^4$ is OH.

5. A compound of claim 1 wherein $(CR^3R^3)_m$ is —$CH_2C(CH_2CH_2)CH_2$—.

6. A compound of claim I selected from the group consisting of:

(R.R)-1-((((3-(2-(7-chloro-2-quinolinyl)-(E)-ethenyl)phenyl)-3-(2-(1,2-dihydroxy-1-methylethyl)phenyl)propyl)thio)methyl)cyclopropane acetic acid;

(R.S)-1-((((3-(2-(7-chloro-2-quinolinyl)-(E)-ethenyl)phenyl)-3-(2-(1,2-dihydroxy-1-methylethyl)phenyl)propyl)thio)methyl) cyclopropaneacetic acid;

1-((((3-(2-(7-Chloro-2-quinolinyl)-(E)-ethenyl)phenyl)-(1R.3S)-3-(2-(1-hydroxy-1-methylethyl)phenyl)-3-hydroxypropyl)thio)methyl) cyclopropaneacetic acid; and 1-((((3-(2-(7-Chloro-2-quinolinyl)-(E)-ethenyl)phenyl)-(1R.3R)-3-(2-(1-hydroxy- 1-methylethyl)phenyl)-3-hydroxypropyl)thio)methyl) cyclopropaneacetic acid.

7. A pharmaceutical composition comprising a thereapeutically effective amount of a compound of claim 1 and a pharmaceutically acceptable carrier.

8. A method of treating asthma in a mammal comprising administering to a mammal in need of such treatment a therapeutically effective amount of a compound of claim 1.

* * * * *